US007066933B2

(12) United States Patent
Hagg

(10) Patent No.: US 7,066,933 B2
(45) Date of Patent: Jun. 27, 2006

(54) HIGH-FREQUENCY GENERATOR FOR PERFORMING HIGH-FREQUENCY SURGERY HAVING ADJUSTABLE POWER LIMITATION, AND METHOD FOR CONTROLLING THE POWER LIMITATION

(75) Inventor: Martin Hagg, Wannweil (DE)

(73) Assignee: Erbe Elektromedizin GmbH, Tubingen (DE)

( * ) Notice: Subject to any disclaimer, the term of this patent is extended or adjusted under 35 U.S.C. 154(b) by 97 days.

(21) Appl. No.: 10/344,422

(22) PCT Filed: Aug. 8, 2001

(86) PCT No.: PCT/EP01/09184

§ 371 (c)(1),
(2), (4) Date: Jun. 18, 2003

(87) PCT Pub. No.: WO02/11634

PCT Pub. Date: Feb. 14, 2002

(65) Prior Publication Data

US 2004/0030329 A1 Feb. 12, 2004

(30) Foreign Application Priority Data

Aug. 8, 2000 (DE) .................. 100 38 687
Sep. 7, 2000 (DE) .................. 100 44 189
Nov. 6, 2000 (DE) .................. 100 54 963

(51) Int. Cl.
*A61B 18/18* (2006.01)

(52) U.S. Cl. ................................. 606/34
(58) Field of Classification Search ............ 606/32–34, 606/37–41, 45–50

See application file for complete search history.

(56) References Cited

U.S. PATENT DOCUMENTS 4,727,874 A 3/1988 Bowers et al.

(Continued)

FOREIGN PATENT DOCUMENTS

DE 35 31 576 5/1986

(Continued)

*Primary Examiner*—Michael Peffley
(74) *Attorney, Agent, or Firm*—Bell Boyd & Lloyd LLC

(57) ABSTRACT

The invention relates to an HF generator and to a method for limiting the output effective power of the HF generator, especially for performing HF surgical cutting and coagulation of human or animal tissue. According to the invention, the output voltage and the HF output current of the HF generator are detected by at least two detector devices, the peak values and the effective values of the HF output voltage and of the output current as well as the mean value of the output effective power of the HF generator are determined by an evaluation device, and the calculated mean value is compared to a defined maximum mean value of the output effective power of the HF generator by a comparison device. Afterwards, a modulation device modulates the HF output voltage using a pulse-shaped modulation signal. A control device controls the modulation device in such a manner that the pulse duration of the pulse-shaped modulation signal and/or the pulse duration between the pulse-shaped modulation signals is modified in order to keep the peak value of the output voltage constant when the calculated mean value of the output effective power is greater than the maximum mean value of the output effective power. Alternatively, the HF generator is equipped with a sensor for evaluating the intensity of electric arcs between an electrode connected to the HF generator and the tissue.

22 Claims, 3 Drawing Sheets

U.S. PATENT DOCUMENTS

| | | | |
|---|---|---|---|
| 5,108,391 A | * 4/1992 | Flachenecker et al. | 606/38 |
| 5,372,596 A | * 12/1994 | Klicek et al. | 606/35 |
| 5,472,443 A | * 12/1995 | Cordis et al. | 606/48 |
| 5,971,980 A | 10/1999 | Sherman | |

FOREIGN PATENT DOCUMENTS

| | | |
|---|---|---|
| DE | 36 22 337 C2 | 1/1988 |
| DE | 38 15835 | 11/1989 |
| DE | 91 17190 | 11/1996 |
| DE | 197 57720 | 6/1999 |
| EP | 1 053 720 A1 | 11/2000 |

* cited by examiner

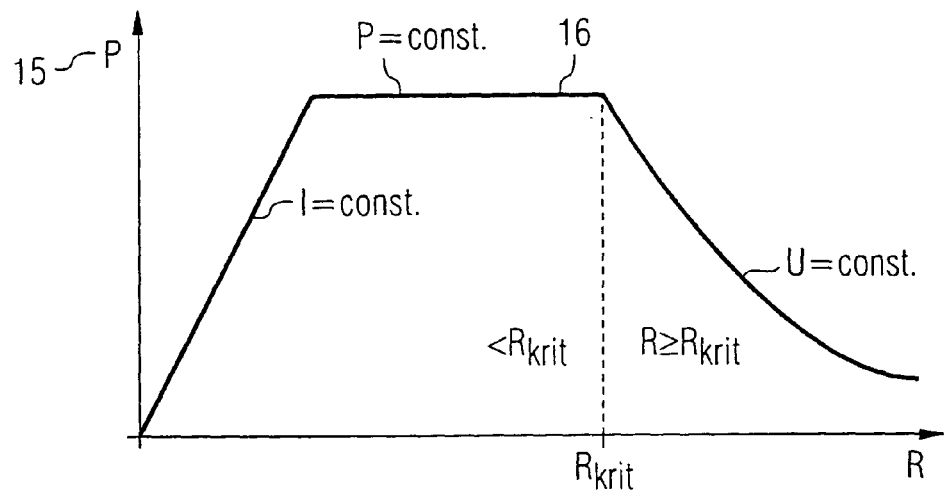
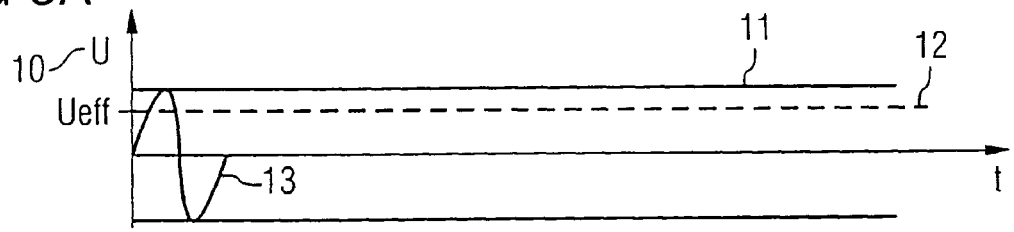
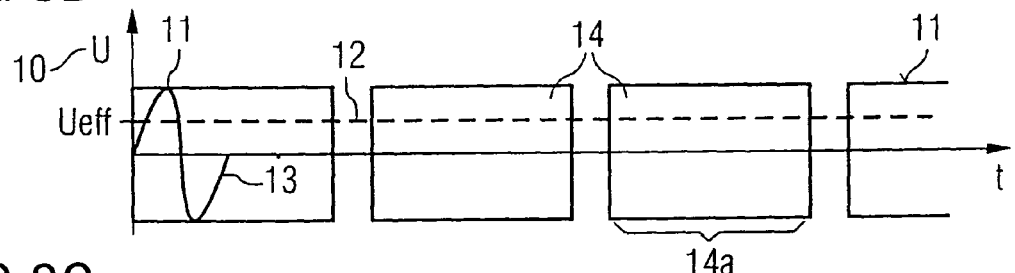
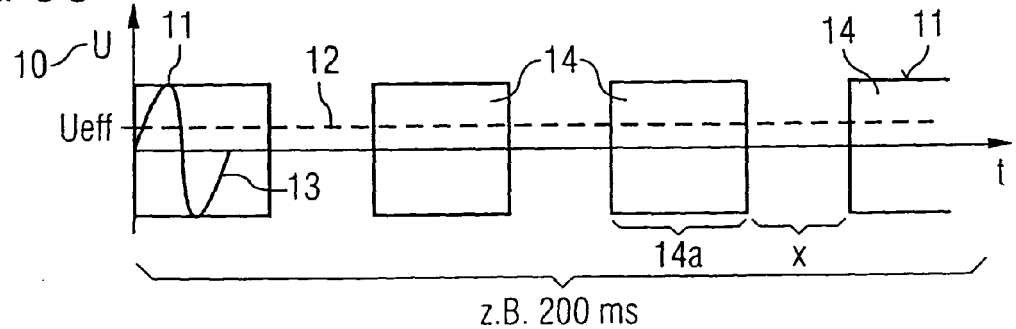

HIGH-FREQUENCY GENERATOR FOR PERFORMING HIGH-FREQUENCY SURGERY HAVING ADJUSTABLE POWER LIMITATION, AND METHOD FOR CONTROLLING THE POWER LIMITATION

BACKGROUND

The present invention relates to a high-frequency (HF) generator with an adjustable means of limiting the effective output power, intended in particular for HF surgical procedures including the cutting and coagulation of human or animal tissue, and also relates to a method of limiting the output power of the high-frequency generator.

In high-frequency surgery, the HF generators used for cutting and coagulating human or animal tissue are distinguished by the fact that they provide a HF voltage which, when applied to an electrode, produces an electrical arc between electrode and tissue that has the effect of making an incision in the tissue. The HF voltages between electrode and tissue that are required for this purpose have a minimal value of ca. 200 Vp (volt peak). During such cutting and coagulation, the voltage applied between the electrode and the tissue has a decisive influence on the amount of coagulation at the edges of the incision. To keep the coagulation degree constant, HF generators are provided with a control circuit that regulates the HF output voltage from the HF generator, and hence the intensity of the electrical arc between electrode and tissue, so as to maintain a constant voltage or intensity level.

The effective output power, which depends on the output voltage of the HF generator, is given by the equation $$P = \frac{U^2}{R}$$

and hence is also a function of the load impedance R. If the load impedance is reduced, owing for instance to a large incision area, the result is that the output voltage U can be kept constant only for as long as the HF generator can generate the necessary effective output power. As soon as the HF generator reaches its power limit, it is no longer capable of maintaining the desired constancy of the output voltage U or the intensity of the electrical arc. This is the case in particular when the effective output power (or output current) of the HF generator reaches a maximum, i.e. an upper limit that has been specified by a prior adjustment process.

For the cutting and coagulation effect, the peak value of the output voltage is particularly crucial. As is well known, the peak value of the HF voltage must reach at least 200 V, so as to ignite the electrical arc required in order to achieve the cutting effect.

In known HF generators the HF output voltage is automatically reduced when the prespecified maximal output power is reached or exceeded, so that the effective output power of the generator does not increase beyond the generator's power limit. At the same time, however, an effort should be made to keep constant the peak value of the output voltage, and hence the intensity of the electrical arc, so that the output voltage will have a largely constant influence on the degree of scab production at the edges of the incision.

SUMMARY

The teachings of the present invention make available a HF generator for the surgical cutting and coagulation of tissue, as well as a method of limiting the effective output power thereof, that make it possible to keep the degree of scab production at the edges of the incision substantially constant even in the case of large-area, deep and/or extremely rapid cutting.

Preferably in the HF generator, and in the method for limiting the effective output power thereof, the generator's output voltage and HF output current are detected and these values are used to calculate the mean effective output power, which is then compared with the previously specified, adjustable maximal mean value of the effective output power, and if the calculated mean is found to be greater than the preset maximal mean value, the HF output voltage is modulated by means of a pulsed modulation signal. The duration of the modulation pulses and/or the duration of the intervals between them are/is preferably adjusted such that the peak value of the HF output voltage, and hence the intensity of the electrical arc, is kept constant. Because the modulation signal subdivides the voltage supply into pulses, the mean effective value of the HF output voltage is reduced as the duration of the intervals separating the individual pulses is increased; as a result, the effective output power of the HF generator is also reduced, and thus the HF generator is advantageously kept within its power limits.

For further details regarding the procedure for keeping the intensity of the arc constant, reference is made to the applicant's unexamined German applications DE 198 39 826 A1 and DE 38 05 291 A1.

At the same time, the peak value of the HF output voltage, and hence the intensity of the arc within the duration of the pulse, is kept at a constant level, as a result of which the degree of coagulation at the incision edges can be made to remain the same even if the load impedance becomes reduced.

Alternatively, the mean value of the effective output power can also be calculated on the basis of the power delivered from the mains supply and a known value for the efficiency of the HF generator.

Instead of a reduction in the degree of coagulation such as occurs when the load impedance becomes less owing to very deep or rapid cutting or the like, the surgeon will detect a mechanical resistance to progress of the electrode, inasmuch as a pulsed signal appears or the existing pulses become separated by longer intervals. As a result, although the cutting movement is slowed down, the desired degree of coagulation at the edges of the incision is still maintained.

This mechanical resistance, in combination with the preservation of the desired degree of coagulation, makes it impossible to carry out the cutting movement too rapidly, which ensures sufficiently good coagulation at the incision edges and consequently a cessation of bleeding.

So that the evaluation device can accurately calculate the mean effective output power, the phase shift between the output voltage and the output current is also measured and taken into account.

Preferably the duration of the pulses or the intervals between them is allowed to change by no more than a specified amount, because a device is provided that imposes a minimal and a maximal permissible pulse duration or interval duration. This measure ensures, firstly, that no HF output voltage is produced with a pulse duration so short that the cutting effect is thereby impaired. Secondly, the imposition of a maximal pulse duration ensures that the pulsed output voltage produced by the modulation signal never exceeds a continuously oscillating HF output voltage.

So as to obtain an effectively regulated HF generator and a method of limiting the effective output power of the HF generator that can be practically implemented, the peak values of the HF output voltage, or the intensity of the electrical arc, and the maximal permissible duration of the pulses and/or intervals are specified at the outset by an initialization device, before the control circuit is put into operation.

A mains power supply, which provides the HF generator with more power as soon as the calculated mean effective output power becomes the same as or greater than the specified and preset maximal mean value, is preferably connected to the control device. This arrangement allows compensation for the generator's internal resistance while simultaneously keeping the peak value of the HF output voltage at the same level.

It is advantageous for the durations of pulses or intervals between pulses to be within a range from 3 μs (at 330 kHz) to 200 ms, so as to ensure that the effects described above regarding the minimal and maximal permissible pulse and/or interval durations are achieved.

It is also possible to lower the set point in the HF generator that governs the peak HF output voltage, and hence the intensity of the arc, whenever the pulse duration falls below the minimal permissible duration. As a result, at the next cycle through a control circuit in the HF generator it is possible effectively to regulate the limitation on the effective output power of the HF generator, in such a way that the process of cutting through the tissue can be continued.

However, the set point for the peak value of the HF output voltage, or the intensity of the electrical arc, can also be raised, namely when the calculated mean value is below the specified maximal mean effective output power, and when the set point has a value smaller than a pre-adjusted peak value. By this means the control circuit of the HF-generator can be readjusted, as far as the upper power limit of the generator.

If the set point is above the prespecified peak value, the pulse duration is increased, as long as it remains below the maximal permissible pulse duration.

In case the maximal effective output power of the generator is limited, by a prior adjustment, to a level below the generator's actual power limit, the effective output power of the HF generator is indicated as a mean effective power value, obtained by averaging over an integration time. This integration time can be equal to the modulation period, i.e. the duration of one modulation cycle, or can be an integral multiple thereof.

It is also advantageous for the effective output power to be calculated on the basis of the output power of the mains power supply and the efficiency of the HF generator.

Additional details, advantages and further developments of the invention will be evident from the following description of an exemplary embodiment with reference to the drawings, wherein

BRIEF DESCRIPTION OF THE SEVERAL VIEWS OF THE DRAWINGS

FIG. 2 is a plot to illustrate the relationship between the effective output power of the HF generator and the load impedance R, FIGS. 3A–3C comprise diagrams in which the HF output voltage of the HF generator is plotted as a function of time for various pulse durations.

DETAILED DESCRIPTION OF THE PREFERRED EXAMPLES

Figure 1:
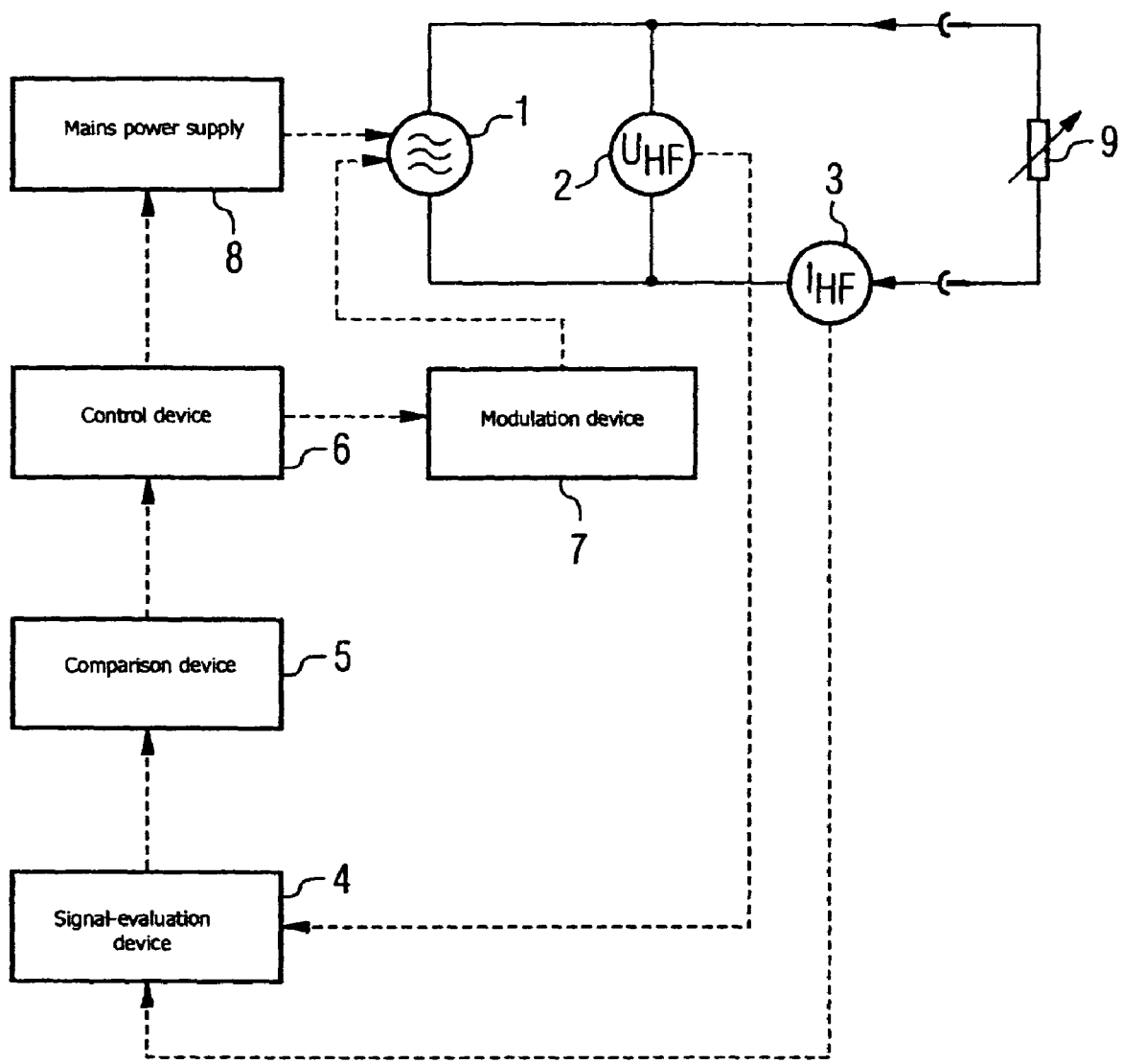
FIG. 1 is a schematic diagram of an exemplary embodiment of the HF generator.

FIG. 1 shows schematically an exemplary embodiment of the HF generator that comprises, in addition to the HF generator 1 itself, two detector devices 2, 3 with which to measure the output voltage or output current of the HF generator 1. For this purpose, the detector devices 2, 3 are constructed as sensors, namely a voltage sensor disposed in parallel with the HF generator 1 and a current-intensity sensor 3 in series with the HF generator 1 and with a load impedance 9.

The sensors 2 and 3 are both connected to an evaluation device 4, which evaluates the sensor signals in order to find the peak and/or effective values of the HF output voltage and the peak and/or effective values of the output current. After these values have been obtained, the evaluation device calculates the mean effective output power of the HF generator, by multiplying the effective value of the HF voltage by that of the HF current and by a cosine function of an additionally measured phase angle between the HF output voltage and the HF output current.

Subsequently the mean value so calculated is sent to a comparison device 5, where it is compared with a previously specified and preset maximal mean value for the effective output power of the HF generator, to determine whether the calculated mean value is larger or smaller than the maximal mean value.

The modulation device 7 then produces a pulsed modulation signal to modulate the output voltage of the HF generator 1 whenever the calculated output power exceeds the preset reference value for the output power.

If the calculated mean value is greater than the maximal mean value, a control device 6 is activated, which controls the modulation device 7 for modulating the output voltage with a pulsed modulation signal. The control is such that the duration of the pulses in the modulation signal is reduced in order to obtain, so to speak, a "dilution" of the output voltage. In this process the pulse duration is lowered by whatever amount is necessary in order to keep constant the peak value of the output voltage.

The control device 6 simultaneously controls a mains power source 8 that supplies the HF generator 1. Hence it is additionally possible to alter the input power signals to the HF generator so as, for example, to bring about compensation for the generator's internal resistance.

In FIG. 2 the time course of the effective output power 15 is shown as a function of the load impedance. In this diagram it is evident that above a critical load impedance $R_{crit}$ the HF generator does not reach its power limit, so that the peak value of the output voltage of the HF generator can be kept constant. This applies likewise to the state in which the load impedance R coincides exactly with the value of the critical impedance $R_{crit}$.

However, as soon as the load impedance R becomes smaller than the critical load impedance $R_{crit}$, the HF generator comes up to the limit of the power it can produce, i.e. its maximal power 16. Therefore, in accordance with the invention, the effective output power of the HF generator is kept constant at a maximal permissible value 16 in that the ratio of peak value to effective value of the output voltage of the HF generator (the "crest factor") is appreciably changed as the load impedance becomes smaller.

In FIG. 3 this variability in the ratio of peak to effective values of the output voltage signals is explained in greater detail by three diagrams. The three diagrams A, B, C differ from one another inasmuch as diagram A shows the time course of a continuously oscillating HF output voltage, whereas in diagrams B and C the output voltage oscillation is subdivided into pulses, the durations of which are different in the two diagrams.

The continuously oscillating HF output voltage 13 shown in diagram A, for a load impedance above $R_{crit}$, has a peak value 11 and an effective value 12. When this continuously oscillating signal is modulated, in the case of load impedances below $R_{crit}$, the effective value 12 of the HF output voltage is reduced while the peak value 11 of the HF output voltage remains the same as previously, as shown for instance in diagram B. The pulses 14 in the modulation signal in diagram B have a duration 14a, which would be the case when the load impedance is only slightly below $R_{crit}$.

In diagram C the modulation signal has a pulse duration (14a) applicable to a load impedance R that has been still further reduced. The effective value 12 of the HF output voltage has become even lower than before, whereas the peak value 11 still remains constant within an oscillation pulse having the specified duration. With such a combination of lowered effective value and constant peak value, on the basis of the crest factor it is possible for the effective output power to be kept below a specified mean value.

The diagrams A, B and C show the time course of the HF output voltage 10 over a time period of 200 ms, from which it can be discerned that the pulse durations are preferably within a range from 3 µs (at 330 kHz) to 200 ms.

Figure 4:
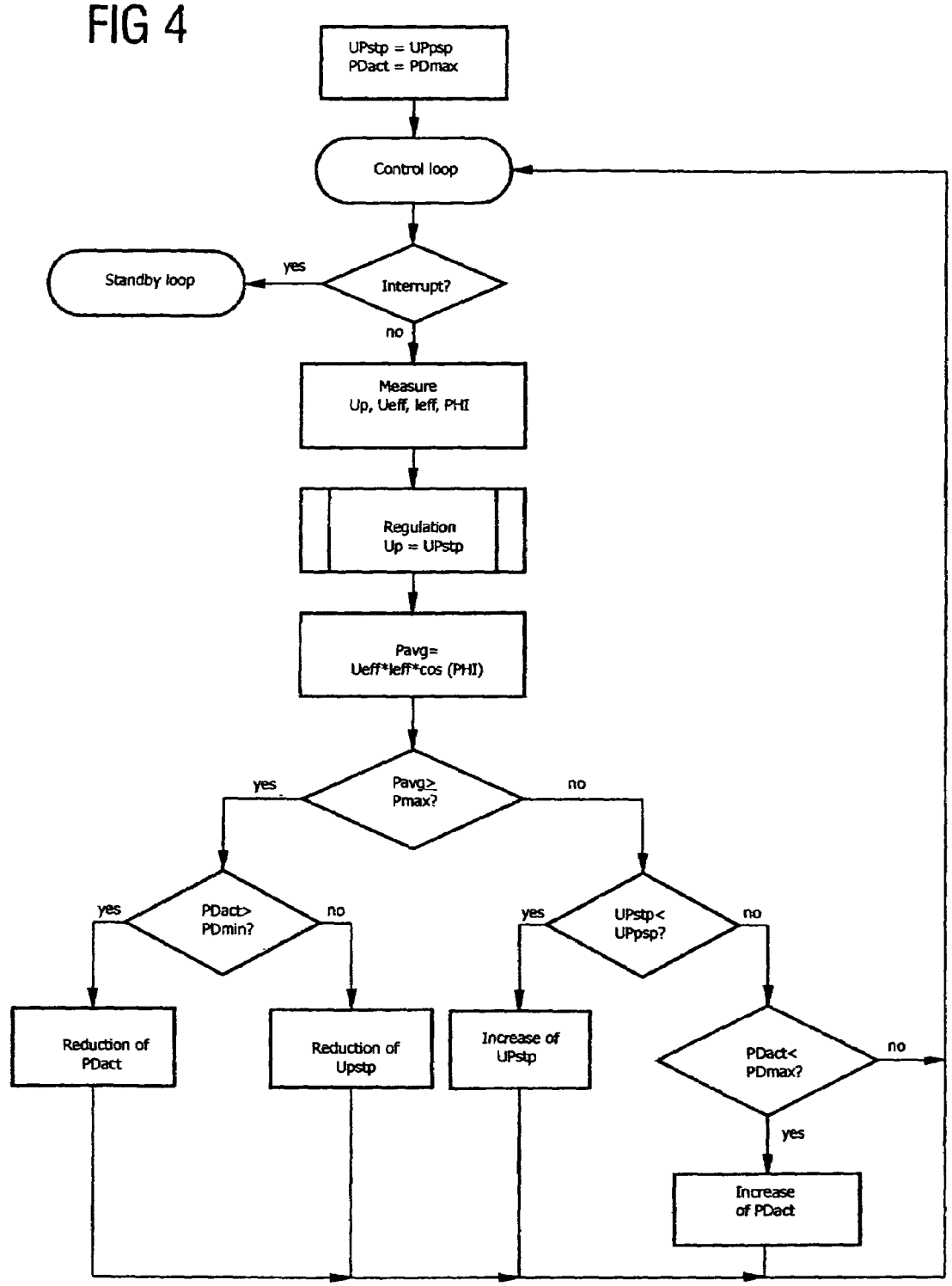
FIG. 4 is a flow diagram of the control circuit of the HF generator and of an exemplary embodiment of the method.

FIG. 4 shows a flow diagram representing the sequence of events in the control circuit associated with the HF generator and with the method.

Before the actual control circuit (loop) is entered, by means of an initialization device the parameter UPpsp, which prespecifies the desired peak value of the HF output voltage to achieve the desired regulation of the generator, is used to initialize a set-point value UPspt to be used during this regulation.

The maximal permissible pulse duration, PDmax, likewise serves to initialize the actual pulse duration, PDact. If the user does not want the output voltage to be modulated by dividing it into pulses, but rather is aiming for a continuous, unmodulated output voltage, then PDmax can be made equal to the period of the voltage oscillation.

Once the actual control circuit has come into operation, it can be inactivated, for example by releasing a finger switch. Insofar as such inactivation does not occur, by means of the detector devices 2, 3 and the signal-evaluation device 4 the peak value Up and the effective value Ueff of the output voltage are measured, as also are the effective value Ieff of the output current and the phase angle PHI between the output voltage and the output current intensity.

Then the peak value Up of the output voltage is regulated to the set point UPspt of the HF output voltage. In a subsequent step the mean value Pavg of the effective output power of the HF generator over at least one cycle of the modulated signal is calculated by multiplying together the effective values of the HF output voltage and the output current, with the cosine of the phase angle PHI, and in a further step this calculated mean value Pavg is compared with a previously specified maximal mean value Pmax.

Whenever the maximal mean value Pmax is exceeded by the calculated mean value Pavg, the result is an incremental reduction of the momentary pulse duration PDact, or if the output is not currently being modulated, then a pulsed modulation signal with the appropriate pulse duration begins to be applied. In the process, the duration of the shortened pulses must not be allowed to fall below a minimal permissible value PDmin. If a reduction would cause the pulse duration to become less than PDmin, then instead of reducing the pulse duration a reduction of the peak-voltage set point UPspt is carried out, after which there is another cycle through the control loop.

If the calculated mean value Pavg is no greater than the maximal mean value Pmax of the effective output power, the set point UPspt for the HF output voltage is incrementally increased as long as it remains smaller than the prespecified value UPpsp. But if an increased UPspt would exceed UPpsp, the pulse duration PDact is increased instead, insofar as it is below the maximal pernissible pulse duration PDmax.

Regardless of whether the set point UPspt of the HF output voltage is raised or lowered, or the pulse duration PDact is raised or lowered, the cycles through the control loop are repeated until the desired effect is achieved, namely the limitation of the effective output power of the HF generator to a maximal permissible value while the peak value of the HF output voltage is kept the same.

The modulation of the HF output voltage by means of a pulsed modulation signal can be programmed in an alternative manner; that is, the onset of modulation or alteration of its pattern can be triggered when a particular value of the load impedance has been reached, rather than the maximal mean value of the effective output power. For this purpose the value of the load impedance is continuously measured and evaluated.

The method in accordance with the invention for limiting the effective output power of a HF generator, as well as the HF generator designed for implementing the method, are particularly suitable for use in HF surgery involving the cutting and coagulation of human or animal tissue. However, it is also conceivable for the method and the generator to be employed in any of the ways that HF generators can be used in other areas of medicine or related fields.

At this juncture it should be pointed out that all the parts described above, in particular the details shown in the drawings, are claimed as essential to the invention in themselves individually as well as in every combination. Modifications thereof are familiar to those skilled in the art.

The invention claimed is:

1. High-frequency generator with adjustable limitation of the effective output power for HF surgical cutting of human or animal tissue, comprising:
   a device for finding the mean value of the effective output power of the HF generator,
   a comparison device for comparing the mean value thus found for the effective output power with a specified maximal mean value of the effective output power of the HF generator,
   a modulation device for modulating the output voltage of the HF generator with a modulation signal comprising pulses, such that a control device for controlling the modulation device alters the duration of the pulses in the modulation signal and/or the duration of the intervals between the pulses, in order to keep constant the peak value of the output voltage or the intensity of an arc that is formed between an electrode connected to the HF generator and the tissue, whenever the mean value found for the effective output power is greater than the maximal mean value of the effective output power.

2. High-frequency generator as claimed in claim 1, wherein at least two detector devices are disposed so as to detect the output voltage and output current of the HF generator, and that the device for finding the mean value of the effective output power is constructed as an evaluation device and the peak or effective values of the output voltage and the peak or effective values of the output current are measured and used to calculate the mean value of the effective output power.

3. High-frequency generator as claimed in claim 1 wherein the control device comprises a limiting device to limit the range of alteration of the pulse duration so that it lies between a minimal permissible pulse duration and a maximal permissible pulse duration-and/or to keep the duration of the inter-pulse interval between a minimal permissible interval duration and a maximal permissible interval duration.

4. High-frequency generator as claimed in claim 1, wherein the device measures the phase shift between the output voltage and the output current.

5. High-frequency generator as claimed in claim 1, wherein an initialization device is so constructed that it initializes prespecified peak values of the output voltage and the maximal permissible pulse duration and/or interval duration to produce set points for the HF generator.

6. High-frequency generator as claimed in claim 1, wherein the control device is in controlling communication with a mains power supply that is so constructed that the HF generator is supplied with higher power when the mean value found for the effective output power is greater than the specified maximal mean value of the effective output power.

7. High-frequency generator as claimed in claim 1, wherein the pulse duration and/or the interval duration is in a range from 3 µs to 200 ms.

8. High-frequency generator as claimed in claim 1, wherein the control device is connected to a load impedance on the output side.

9. High-frequency generator as claimed in claim 1, wherein at least one arc-detector is present to detect the intensity of the electrical arc that is formed between the electrode connected to the HF generator and the tissue.

10. High-frequency generator as claimed in claim 1, wherein the integration time for finding the mean values of the effective output power or the effective values of the output voltage and/or the output current of the high-frequency generator corresponds to integral multiples of the modulation cycle duration, i.e. the duration of one pulse plus the duration of one interval, but in any case corresponds to at least the duration of a single modulation cycle.

11. Method for limiting the effective output power of a high-frequency (HF) generator for HF surgical cutting and coagulation of human or animal tissue, comprising:
finding the mean value of the effective output power of the HF generator by means of a specially designed device,
comparing the mean value found for the effective output power with a specified maximal mean value of the effective output power of the HF generator by means of a comparison device,
modulating the output voltage of the HF generator with a modulation signal comprising pulses, by means of a modulation device, and
controlling the modulation device—by means of a control device in such a way that the duration of the pulses in the modulation signal and/or the duration of the intervals between the pulses are/is altered in order to keep constant the peak value of the output voltage and hence the intensity of an arc that is formed between an electrode connected to the HF generator and the tissue, whenever the mean value found for the effective output power is greater than the maximal mean value of the effective output power.

12. Method according to claim 11, comprising the step of detecting the output voltage and the output current of the HF generator by means of at least two detector devices and finding the peak or effective values of the output voltage and the peak or effective values of the output current by means of the device for finding such values, here employed as an evaluation device.

13. Method as claimed in claim 11, comprising the step of limiting the range of alteration of the pulse duration so that it lies between a minimal permissible pulse duration and a maximal permissible pulse duration and/or keeping the duration of the interval between pulses between a minimal permissible interval duration and a maximal permissible interval duration.

14. Method as claimed in claim 11, comprising the step of measuring the phase shift between the output voltage and the output current in order to calculate the mean value of the effective output power.

15. Method as claimed in claim 11 comprising the step of initializing a prespecified peak value of the output voltage and the maximal permissible pulse duration and/or interval duration to produce set points.

16. Method as claimed in claim 15, comprising the step of altering the set point for the peak value of the output voltage when the pulse duration is not greater than the minimal permissible pulse duration.

17. Method as claimed in claim 15, comprising the step of altering the set point for the peak value of the output voltage when the average value found for the effective output power is smaller than the specified maximal mean value thereof, and when the set point is smaller than the prespecified peak value.

18. Method as claimed in claim 15, comprising the step of altering the pulse duration when the existing mean value is smaller than the specified maximal mean value of the effective output power, and when the set point is not smaller than the prespecified peak value, and when the pulse duration is smaller than the maximal permissible pulse duration.

19. Method as claimed in claim 11 comprising the step of controlling a mains power device by means of the control device in such a way that the mains power device—supplies the HF generator with higher power when the existing mean value is the same as or larger than the specified maximal mean value of the effective output power.

20. Method as claimed in claim 11, wherein the pulse duration and/or the interval duration is in a range from 3 µs to 200 ms.

21. Method as claimed in claim 17, further comprising the step of detecting an intensity of an electrical arc that is formed between an electrode connected to the HF generator and the tissue, by means of at least one arc-detector device.

22. Method as claimed in claim 11, wherein the integration time for finding the mean values of the effective output power or the effective values of the output voltage and/or the output current of the high-frequency generator corresponds to integral multiples of the modulation cycle duration.

* * * * *